(12) United States Patent  
Den Boef et al.

(10) Patent No.: US 7,791,727 B2
(45) Date of Patent: Sep. 7, 2010

(54) METHOD AND APPARATUS FOR ANGULAR-RESOLVED SPECTROSCOPIC LITHOGRAPHY CHARACTERIZATION

(75) Inventors: Arie Jeffrey Den Boef, Waalre (NL); Mircea Dusa, Campbell, CA (US); Antoine Gaston Marie Kiers, Veldhoven (NL); Maurits Van Der Schaar, Veldhoven (NL)

(73) Assignee: ASML Netherlands B.V., Veldhoven (NL)

( * ) Notice: Subject to any disclaimer, the term of this patent is extended or adjusted under 35 U.S.C. 154(b) by 769 days.

(21) Appl. No.: 10/918,742

(22) Filed: Aug. 16, 2004

(65) Prior Publication Data

US 2006/0033921 A1    Feb. 16, 2006

(51) Int. Cl.
*G01B 9/02*    (2006.01)
*G01B 11/00*    (2006.01)

(52) U.S. Cl. .................................. 356/401; 356/521
(58) Field of Classification Search ................ 356/401, 356/490, 515, 521; 250/237 G
See application file for complete search history.

(56) References Cited

U.S. PATENT DOCUMENTS

| | | | |
|---|---|---|---|
| 3,909,602 A | 9/1975 | Micka | |
| 4,538,914 A | 9/1985 | Yomoda et al. | |
| 4,672,196 A | 6/1987 | Canino | |
| 4,999,014 A * | 3/1991 | Gold et al. | 356/632 |
| 5,042,951 A * | 8/1991 | Gold et al. | 356/369 |
| 5,153,669 A | 10/1992 | DeGroot | |
| 5,166,752 A * | 11/1992 | Spanier et al. | 356/369 |
| 5,192,980 A | 3/1993 | Dixon et al. | |
| 5,218,415 A | 6/1993 | Kawashima | 356/152 |
| 5,349,440 A | 9/1994 | DeGroot | |
| 5,412,473 A * | 5/1995 | Rosencwaig et al. | 356/451 |
| 5,541,731 A | 7/1996 | Freedenberg et al. | |
| 5,596,411 A | 1/1997 | Fanton et al. | |
| 5,703,692 A * | 12/1997 | McNeil et al. | 356/445 |
| 5,713,364 A | 2/1998 | DeBaryshe et al. | |
| 5,771,094 A | 6/1998 | Carter et al. | |
| 5,877,859 A | 3/1999 | Aspnes et al. | |
| 5,880,838 A * | 3/1999 | Marx et al. | 356/498 |
| 5,910,842 A | 6/1999 | Piwonka-Corle et al. | |
| 5,963,329 A | 10/1999 | Conrad et al. | 356/372 |

(Continued)

FOREIGN PATENT DOCUMENTS

| | | |
|---|---|---|
| EP | 0 396 409 B1 | 3/1998 |
| EP | 0 882 976 A1 | 12/1998 |
| EP | 0 973 069 A2 | 1/2000 |

(Continued)

OTHER PUBLICATIONS

European Search Report issued for European Patent Application No. 05254994.6-2222, dated Feb. 23, 2006.

(Continued)

*Primary Examiner*—Gregory J Toatley, Jr.
*Assistant Examiner*—Scott M Richey
(74) *Attorney, Agent, or Firm*—Sterne, Kessler, Goldstein & Fox P.L.L.C.

(57) ABSTRACT

An apparatus and method to determine a property of a substrate by measuring, in the pupil plane of a high numerical aperture lens, an angle-resolved spectrum as a result of radiation being reflected off the substrate. The property may be angle and wavelength dependent and may include the intensity of TM- and TE-polarized light and their relative phase difference.

32 Claims, 8 Drawing Sheets

U.S. PATENT DOCUMENTS

| | | | |
|---|---|---|---|
| 6,122,051 A | 9/2000 | Ansley et al. | |
| 6,177,994 B1* | 1/2001 | Watson et al. | 356/343 |
| 6,417,916 B1 | 7/2002 | Dengler et al. | |
| 6,429,930 B1 | 8/2002 | Littau et al. | 356/124 |
| 6,429,943 B1* | 8/2002 | Opsal et al. | 356/625 |
| 6,449,037 B2 | 9/2002 | Jun et al. | |
| 6,515,744 B2 | 2/2003 | Wei | 356/369 |
| 6,532,076 B1 | 3/2003 | Sidorowich | 356/630 |
| 6,606,152 B2 | 8/2003 | Littau et al. | 356/124 |
| 6,608,690 B2 | 8/2003 | Niu et al. | 356/635 |
| 6,654,131 B2 | 11/2003 | Opsal et al. | 356/625 |
| 6,699,624 B2 | 3/2004 | Niu et al. | 430/5 |
| 6,704,661 B1 | 3/2004 | Opsal et al. | 702/27 |
| 6,721,691 B2 | 4/2004 | Bao et al. | 702/189 |
| 6,738,138 B2 | 5/2004 | Wei | 356/369 |
| 6,750,968 B2 | 6/2004 | Sandusky | |
| 6,753,961 B1 | 6/2004 | Norton et al. | 356/364 |
| 6,768,983 B1 | 7/2004 | Jakatdar et al. | 706/46 |
| 6,772,084 B2* | 8/2004 | Bischoff et al. | 702/127 |
| 6,775,015 B2* | 8/2004 | Bischoff et al. | 356/636 |
| 6,778,911 B2 | 8/2004 | Opsal et al. | 702/27 |
| 6,781,706 B2 | 8/2004 | Sidorowich | 356/630 |
| 6,785,638 B2 | 8/2004 | Niu et al. | 702/189 |
| 6,791,679 B2 | 9/2004 | Engelhard et al. | 356/124 |
| 6,813,034 B2 | 11/2004 | Rosencwaig et al. | |
| 6,819,426 B2 | 11/2004 | Sezginer et al. | |
| 6,829,057 B2 | 12/2004 | Opsal et al. | |
| 6,842,259 B2 | 1/2005 | Rosencwaig et al. | 356/601 |
| 6,856,408 B2* | 2/2005 | Raymond | 356/601 |
| 6,866,153 B2 | 3/2005 | Turner, Jr. et al. | 210/483 |
| 6,870,621 B2 | 3/2005 | Wei | 356/369 |
| 6,885,464 B1 | 4/2005 | Pfeiffer et al. | 356/602 |
| 6,919,964 B2 | 7/2005 | Chu | 356/601 |
| 6,928,628 B2 | 8/2005 | Seligson et al. | 716/4 |
| 6,931,361 B2 | 8/2005 | Opsal et al. | 702/189 |
| 6,947,850 B2 | 9/2005 | Opsal et al. | 702/27 |
| 6,949,462 B1* | 9/2005 | Yang et al. | 438/650 |
| 6,952,261 B2 | 10/2005 | Ebert et al. | |
| 6,972,852 B2* | 12/2005 | Opsal et al. | 356/625 |
| 6,974,962 B2 | 12/2005 | Brill et al. | 250/548 |
| 6,982,793 B1 | 1/2006 | Yang et al. | |
| 6,987,572 B2 | 1/2006 | Lakkapragada et al. | 356/601 |
| 6,992,764 B1* | 1/2006 | Yang et al. | 356/369 |
| 7,046,376 B2* | 5/2006 | Sezginer | 356/601 |
| 7,061,615 B1 | 6/2006 | Lowe-Webb | 356/401 |
| 7,061,622 B2 | 6/2006 | Rollins et al. | |
| 7,061,623 B2 | 6/2006 | Davidson | |
| 7,061,627 B2* | 6/2006 | Opsal et al. | 356/601 |
| 7,068,363 B2 | 6/2006 | Bevis et al. | |
| 7,080,330 B1 | 7/2006 | Choo et al. | |
| 7,089,164 B2 | 8/2006 | Middlebrooks | |
| 7,112,813 B2 | 9/2006 | Den Boef et al. | |
| 7,115,858 B1 | 10/2006 | Holden et al. | |
| 7,215,431 B2* | 5/2007 | Opsal | 356/630 |
| 7,224,456 B1 | 5/2007 | Phan et al. | |
| 7,230,703 B2 | 6/2007 | Sezinger et al. | |
| 7,236,244 B1 | 6/2007 | Yang et al. | |
| 7,265,850 B2 | 9/2007 | Archie et al. | |
| 7,280,212 B2 | 10/2007 | Mieher et al. | |
| 7,292,341 B2 | 11/2007 | Brill et al. | |
| 7,317,531 B2 | 1/2008 | Mieher et al. | |
| 7,333,200 B2 | 2/2008 | Sezinger et al. | |
| 7,440,105 B2 | 10/2008 | Adel et al. | |
| 7,483,133 B2 | 1/2009 | Bareket et al. | |
| 2002/0018217 A1 | 2/2002 | Weber-Grabau et al. | 356/601 |
| 2002/0165636 A1 | 11/2002 | Hasan | 700/121 |
| 2002/0166982 A1 | 11/2002 | Kataoka et al. | 250/548 |
| 2002/0192577 A1 | 12/2002 | Fay et al. | |
| 2003/0002043 A1 | 1/2003 | Abdulhalim et al. | 356/400 |
| 2003/0081216 A1 | 5/2003 | Ebert et al. | 356/445 |
| 2003/0133102 A1 | 7/2003 | Opsal | 356/237.1 |
| 2003/0143761 A1 | 7/2003 | Fukuda | |
| 2003/0163295 A1 | 8/2003 | Jakatdar et al. | 703/14 |
| 2003/0225535 A1 | 12/2003 | Doddi et al. | 702/76 |
| 2004/0004726 A1 | 1/2004 | Sezginer et al. | 356/601 |
| 2004/0017574 A1* | 1/2004 | Vuong et al. | 356/625 |
| 2004/0066517 A1 | 4/2004 | Huang et al. | 356/509 |
| 2004/0070772 A1* | 4/2004 | Shchegrov et al. | 356/625 |
| 2004/0078173 A1* | 4/2004 | Bischoff et al. | 703/2 |
| 2004/0119970 A1 | 6/2004 | Dusa et al. | |
| 2004/0133362 A1 | 7/2004 | Barouch et al. | 702/28 |
| 2004/0167754 A1* | 8/2004 | Bischoff et al. | 703/2 |
| 2004/0181768 A1 | 9/2004 | Krukar | 716/19 |
| 2004/0190008 A1 | 9/2004 | Mieher et al. | |
| 2004/0196460 A1* | 10/2004 | Dobschal et al. | 356/369 |
| 2004/0201836 A1 | 10/2004 | Chang et al. | 356/237.1 |
| 2004/0223137 A1* | 11/2004 | Littau et al. | 356/123 |
| 2004/0239954 A1* | 12/2004 | Bischoff | 356/635 |
| 2004/0246476 A1 | 12/2004 | Bevis et al. | 356/237.5 |
| 2005/0012928 A1* | 1/2005 | Sezginer et al. | 356/401 |
| 2005/0041258 A1 | 2/2005 | Opsal et al. | 356/601 |
| 2005/0046855 A1 | 3/2005 | Davidson | 356/451 |
| 2005/0106479 A1 | 5/2005 | Geh et al. | |
| 2005/0122516 A1 | 6/2005 | Sezginer et al. | 356/401 |
| 2005/0123844 A1 | 6/2005 | Monshouwer | |
| 2005/0195412 A1* | 9/2005 | Opsal | 356/630 |
| 2005/0209816 A1* | 9/2005 | Vuong et al. | 702/167 |
| 2006/0007446 A1 | 1/2006 | Boef et al. | |
| 2006/0066855 A1* | 3/2006 | Boef et al. | 356/401 |
| 2006/0082792 A1* | 4/2006 | Sezginer | 356/625 |
| 2006/0126074 A1 | 6/2006 | Van Der Werf et al. | |
| 2006/0139592 A1 | 6/2006 | Den Boef et al. | |
| 2006/0243912 A1* | 11/2006 | Raymond et al. | 250/359.1 |
| 2007/0019171 A1* | 1/2007 | Smith | 355/52 |
| 2008/0036984 A1 | 2/2008 | Mos et al. | |
| 2008/0043239 A1 | 2/2008 | Boef et al. | |
| 2008/0074666 A1 | 3/2008 | Boef et al. | |
| 2008/0144036 A1 | 6/2008 | Van Der Schaar | |
| 2008/0239318 A1 | 10/2008 | Boef et al. | |
| 2008/0311344 A1 | 12/2008 | Kiers et al. | |

FOREIGN PATENT DOCUMENTS

| | | |
|---|---|---|
| EP | 1 400 855 A2 | 3/2004 |
| JP | 1-303721 A | 12/1989 |
| JP | 2000-097841 A | 4/2000 |
| JP | 2003-224057 A | 8/2003 |
| WO | WO 95/02814 A1 | 1/1995 |
| WO | WO03065119 A2 | 8/2003 |
| WO | WO 03/075042 A2 | 9/2003 |
| WO | WO2004024328 A1 | 3/2004 |
| WO | W02004053426 A1 | 6/2004 |
| WO | WO 2005/028992 A2 | 3/2005 |
| WO | WO 2005/069082 A1 | 7/2005 |

OTHER PUBLICATIONS

European Search Report issued for EP Patent Application No. 05254994.6, dated Dec. 9, 2005.

Notice of Reasons for Rejection for Japanese Patent Application No. 2005-235188 mailed Mar. 3, 2009, 4 pgs.

English abstract for Japanese publication no. JP 9-504861T published May 13, 1997, 1 pg.

Non-Final Rejection mailed Jun. 20, 2008 for U.S. Appl. No. 11/203,418, 22 pgs.

Final Rejection mailed Apr. 15, 2009 for U.S. Appl. No. 11/203,418, 13 pgs.

J. Bischoff et al., "Light Diffraction Based Overlay Measurement", Metrology, Inspection, and Process Control for Microlithography XV, 2001, vol. 4344, pp. 222-233, Proceedings of SPIE.

Non-Final Rejection mailed Sep. 2, 2009 for U.S. Appl. No. 11/203,418, 14 pgs.

Notice of Allowance mailed Feb. 3, 2010 for U.S. Appl. No. 11/203,418, 10 pgs.

\* cited by examiner

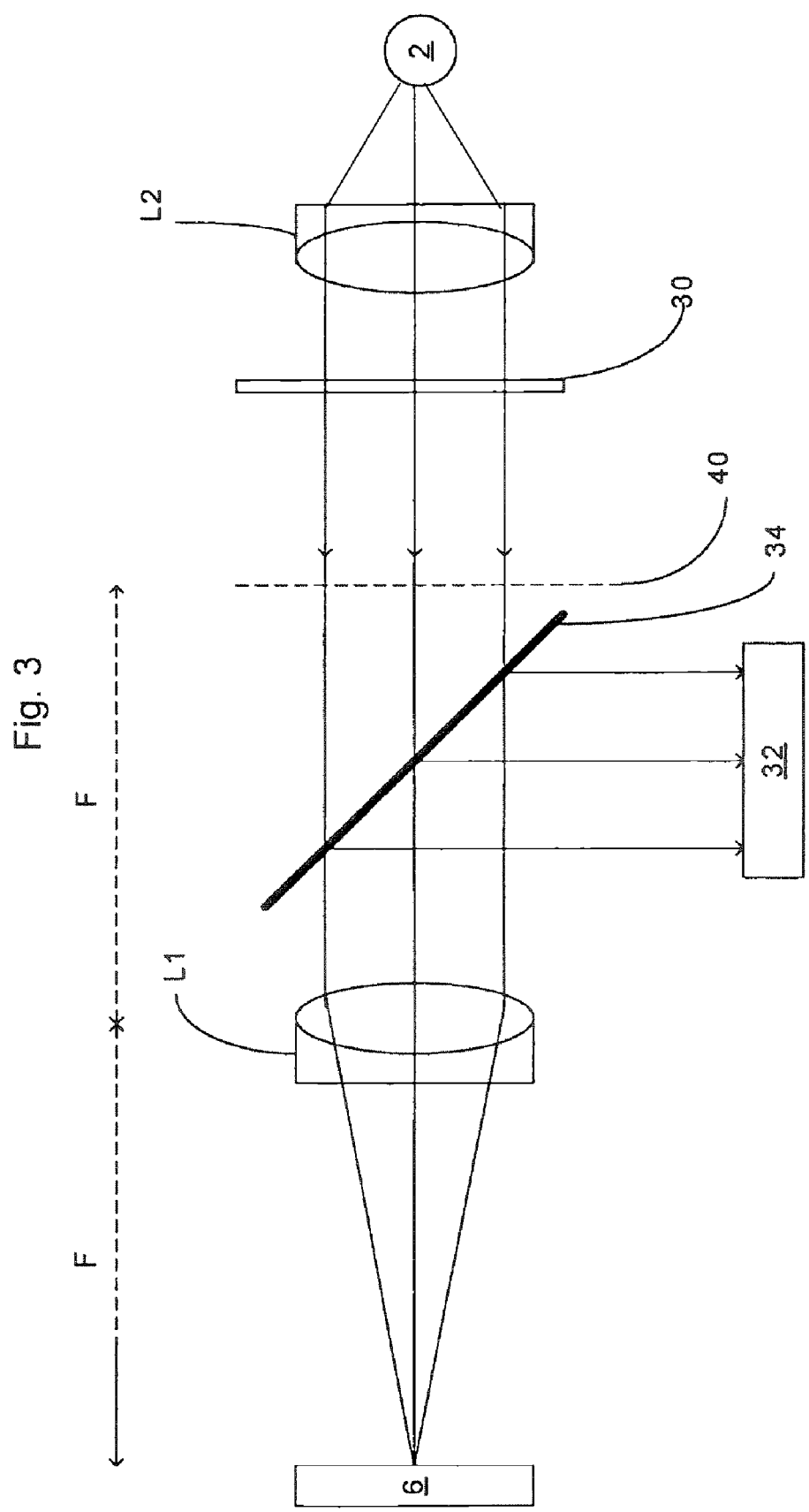

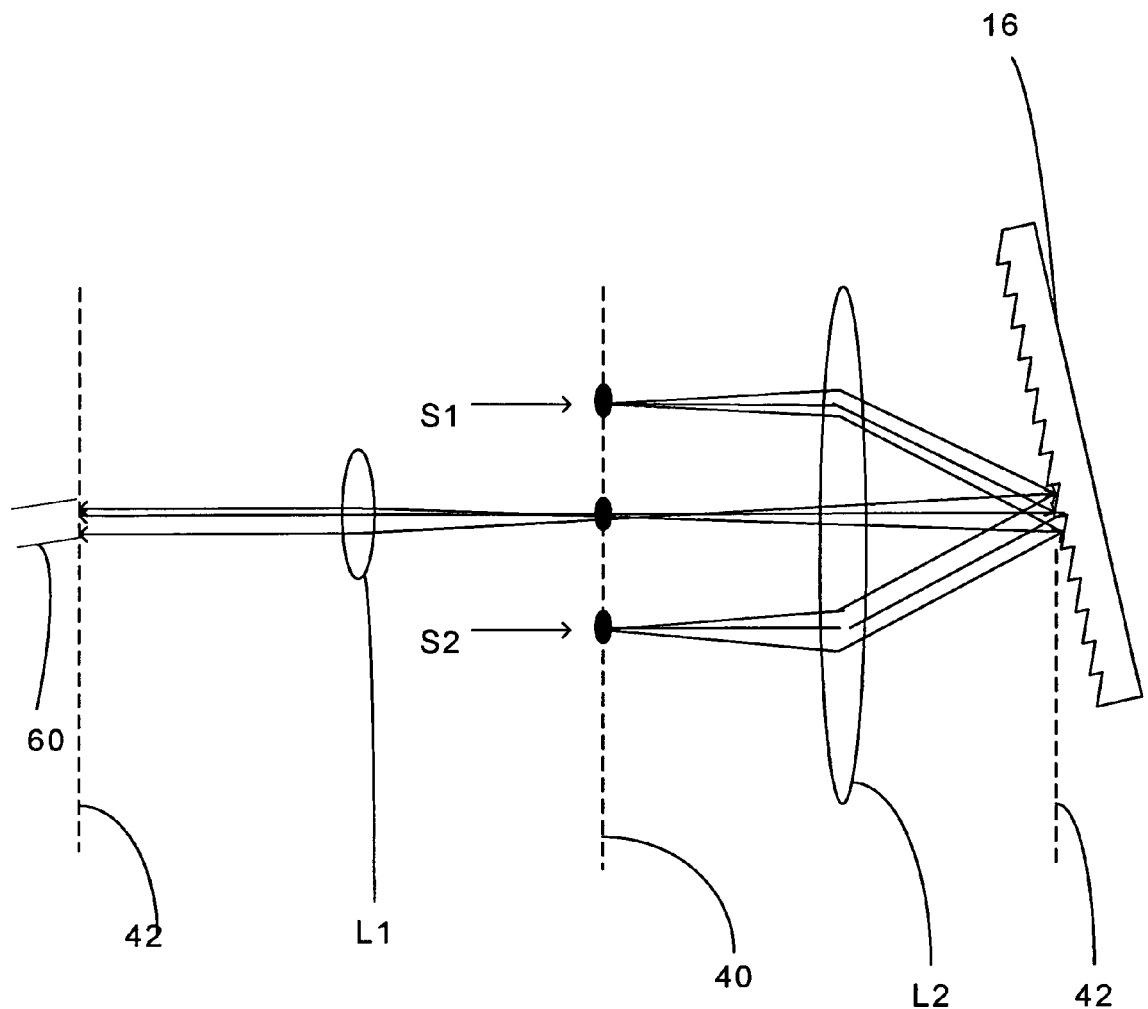

METHOD AND APPARATUS FOR ANGULAR-RESOLVED SPECTROSCOPIC LITHOGRAPHY CHARACTERIZATION

FIELD

The present invention relates to methods of inspection usable, for example, in the manufacture of devices by lithographic techniques and to methods of manufacturing devices using lithographic techniques.

BACKGROUND

In a manufacturing process using a lithographic projection apparatus, a pattern (e.g. in a mask) is imaged onto a substrate that is at least partially covered by a layer of radiation-sensitive material (resist) by the changes of either optical properties or surface physical properties of the resist. Alternatively, the imaging step may use a resistless process such as etched grating or nano-imprint technology. Prior to this imaging step, the substrate may undergo various procedures, such as priming, resist coating and a soft bake. After exposure, the substrate may be subjected to other procedures, such as a post-exposure bake (PEB), development, a hard bake and measurement/inspection of the imaged features. This array of procedures is used as a basis to pattern an individual layer of a device, e.g. an IC. Such a patterned layer may then undergo various processes such as etching, ion-implantation (doping), metallization, oxidation, chemical-mechanical polishing, etc., all intended to finish off an individual layer. If several layers are required, then the whole procedure, or a variant thereof, will have to be repeated for each new layer. Eventually, an array of devices will be present on the substrate (wafer). These devices are then separated from one another by a technique such as dicing or sawing, whence the individual devices can be mounted on a carrier, connected to pins, etc.

The measurement and inspection step after development of the resist (or substrate surface in the case of etching), referred to as in-line because it is carried out in the normal course of processing production substrates, typically serves two purposes. Firstly, it is desirable to detect any target areas where the pattern in the developed resist is faulty. If a sufficient number of target areas are faulty, the substrate can be stripped of the patterned resist and re-exposed, hopefully correctly, rather than making the fault permanent by carrying out a process step, e.g., an etch, with a faulty pattern. Secondly, the measurements may allow errors in the lithographic apparatus, e.g. illumination settings or exposure dose, to be detected and corrected for in subsequent exposures. However, many errors in the lithographic apparatus cannot easily be detected or quantified from the patterns printed in resist. Detection of a fault does not always lead directly to its cause. Thus, a variety of off-line procedures for detecting and measuring errors in the lithographic apparatus are known. These may involve replacing the substrate with a measuring device or carrying out exposures of special test patterns, e.g., at a variety of different machine settings. Such off-line techniques take time, often a considerable amount, during which the end products of the apparatus will be of an unknown quality until the measurement results are made available. Therefore, in-line techniques, ones which can be carried out at the same time as production exposures, for detecting and measuring errors in the lithographic apparatus, are usually preferred.

Scatterometry is one example of an optical metrology technique that can be used for in-line measurements of critical dimension (CD) and overlay. There are two main scatterometry techniques:

(1) Spectroscopic scatterometry measures the properties of scattered light at a fixed angle as a function of wavelength, usually using a broadband light source such as xenon, deuterium, or halogen based light source such as a xenon arc lamp. The fixed angle can be normally incident or obliquely incident.

(2) Angle-resolved scatterometry measures the properties of scattered light at a fixed wavelength as a function of angle of incidence, usually using a laser as a single wavelength light source.

The structure giving rise to a reflected spectrum is reconstructed, e.g., using real-time regression or by comparison to a library of patterns derived by simulation. Reconstruction involves minimization of a cost function. Both approaches calculate the scattering of light by periodic structures. The most common technique is Rigorous Coupled-Wave Analysis (RCWA), though light scattering can also be calculated by other techniques such as Finite Difference Time Domain (FDTD) or Integral Equation techniques.

A problem with known angle-resolved scatterometry techniques is that they only detect one wavelength at a time so spectra with more than one wavelength have to have those wavelengths time-multiplexed, which increases the total acquisition time taken to detect and process the spectra. In spectroscopic scatterometry, an extended light source with a large etendue is used. Since a small grating must be illuminated with a small spread in angle of incidence, a lot of light from this extended source is wasted. This results in low light levels on the detector that lead to long acquisition times, which have a negative impact on throughput. If short acquisition times are chosen, the measurement results might not be stable.

SUMMARY

Accordingly, it would be advantageous, for example, to provide a method of measuring overlay and grating shape parameters (such as grating asymmetry and alignment) during manufacture of devices using lithographic techniques and measurement of an angle-resolved spectrum in a pupil plane of a high NA (numerical aperture) lens. Projection system aberrations, etc. can also be measured in order to be corrected or compensated for.

Embodiments of the present invention may encompass hardware that is capable of measuring angle-resolved spectra at multiple wavelengths simultaneously, of carrying out immersion scatterometry and a focus measurement method for an angle-resolved scatterometer, and of measuring intensity noise of a radiation source with a 2-D detector array. Furthermore, embodiments of the present invention may encompass applications of the hardware including measuring overlay through the measurement of asymmetry of scattered light and measuring small line shape variations via Rayleigh anomalies and high diffraction orders of scattered light.

Although specific reference may be made in this text to the use of the apparatus according to the invention in the manufacture of ICs, it should be explicitly understood that such an apparatus has many other possible applications. For example, it may be employed in the manufacture of integrated optical systems, guidance and detection patterns for magnetic domain memories, liquid-crystal display panels, thin-film magnetic heads, etc. The skilled artisan will appreciate that, in the context of such alternative applications, any use of the terms "reticle", "wafer" or "die" in this text should be considered as being replaced by the more general terms "mask", "substrate" and "target portion", respectively.

In the present document, the terms "radiation" and "beam" are used to encompass all types of electromagnetic radiation, including ultraviolet radiation (e.g. with a wavelength of 365, 248, 193, 157 or 126 nm) and EUV (extreme ultra-violet radiation, e.g., having a wavelength in the range 5-20 nm), as well as particle beams, such as ion beams or electron beams.

BRIEF DESCRIPTION OF THE DRAWINGS

Embodiments of the invention will now be described, by way of example only, with reference to the accompanying schematic drawings in which corresponding reference symbols indicate corresponding parts and in which:

FIG. 3 depicts the general operating principle of measuring an angle-resolved spectrum in the pupil plane of a high NA lens according to an embodiment of the invention;

FIG. 6 depicts a wavelength multiplexer according to an embodiment of the invention;

DETAILED DESCRIPTION

FIG. 1 schematically depicts a lithographic projection apparatus useable in a method according to an embodiment of the invention. The apparatus comprises:

- a radiation system Ex, IL, for supplying a projection beam PB of radiation (e.g. DUV radiation), which in this particular case also comprises a radiation source LA;
- a first object table (mask table) MT provided with a mask holder for holding a mask MA (e.g. a reticle), and connected to a first positioning device for accurately positioning the mask with respect to item PL;
- a second object table (substrate table) WT provided with a substrate holder for holding a substrate W (e.g. a resist-coated silicon wafer), and connected to a second positioning device for accurately positioning the substrate with respect to item PL;
- a projection system ("projection lens") PL (e.g. a refractive lens system) for imaging an irradiated portion of the mask MA onto a target portion C (e.g. comprising one or more dies) of the substrate W.

As here depicted, the apparatus is of a transmissive type (e.g. has a transmissive mask). However, in general, it may also be of a reflective type, for example (e.g. with a reflective mask). Alternatively, the apparatus may employ another kind of patterning device, such as a programmable mirror array of a type as referred to above.

The source LA (e.g. an excimer laser) produces a beam of radiation. This beam is fed into an illumination system (illuminator) IL, either directly or after having traversed conditioning means, such as a beam expander Ex, for example. The illuminator IL may comprise adjusting means AM for setting the outer and/or inner radial extent (commonly referred to as σ-outer and σ-inner, respectively) of the intensity distribution in the beam. In addition, it will generally comprise various other components, such as an integrator IN and a condenser CO. In this way, the beam PB impinging on the mask MA has a desired uniformity and intensity distribution in its cross-section.

Figures 1A, 1B, 1C:
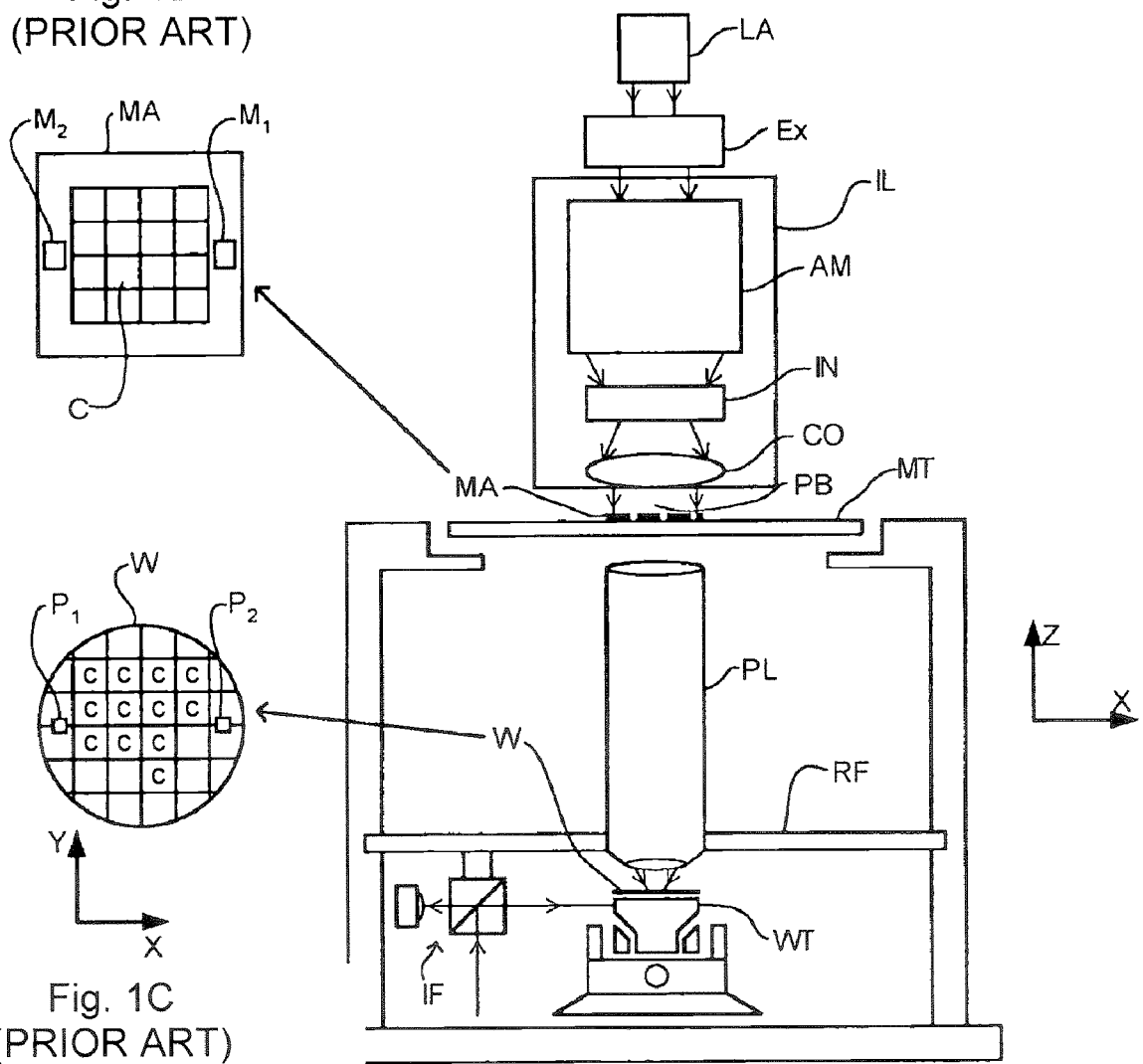
FIG. 1 depicts a lithographic projection apparatus that may be used to perform a method according to an embodiment of the invention.

It should be noted with regard to FIG. 1A that the source LA may be within the housing of the lithographic projection apparatus (as is often the case when the source LA is a mercury lamp, for example), but that it may also be remote from the lithographic projection apparatus, the radiation beam which it produces being led into the apparatus (e.g. with the aid of suitable directing mirrors); this latter scenario is often the case when the source LA is an excimer laser. The current invention and claims encompass both of these scenarios.

The beam PB subsequently intercepts the mask MA, which is held on a mask table MT. FIG. 1B shows an enlarged plan view of the mask MA. Having traversed the mask MA, the beam PB passes through the projection lens PL, which focuses the beam PB onto a target portion C of the substrate W. FIG. 1C shows an enlarged plan view of the substrate W. With the aid of the second positioning device (and an interferometric measuring device IF), the substrate table WT can be moved accurately, e.g. so as to position different target portions C in the path of the beam PB. Similarly, the first positioning device can be used to position the mask MA accurately with respect to the path of the beam PB, e.g. after mechanical retrieval of the mask MA from a mask library, or during a scan. In general, movement of the object tables MT, WT will be realized with the aid of a long-stroke module (coarse positioning) and a short-stroke module (fine positioning), which are not explicitly depicted in FIG. 1. However, in the case of a stepper (as opposed to a step-and-scan apparatus) the mask table MT may just be connected to a short stroke actuator, or may be fixed.

The depicted apparatus can be used in two different modes:

1. In step mode, the mask table MT is kept essentially stationary, and an entire mask image is projected at one time (i.e. a single "flash") onto a target portion C. The substrate table WT is then shifted in the X and/or Y directions so that a different target portion C can be irradiated by the beam PB;

2. In scan mode, essentially the same scenario applies, except that a given target portion C is not exposed in a single "flash". Instead, the mask table MT is movable in a given direction (the so-called "scan direction", e.g. the Y direction) with a speed v, so that the projection beam PB is caused to scan over a mask image; concurrently, the substrate table WT is simultaneously moved in the same or opposite direction at a speed V=Mv, in which M is the magnification of the projection system PL (typically, M=¼ or ⅕). In this manner, a relatively large target portion C can be exposed, without having to compromise on resolution.

Figure 2A:
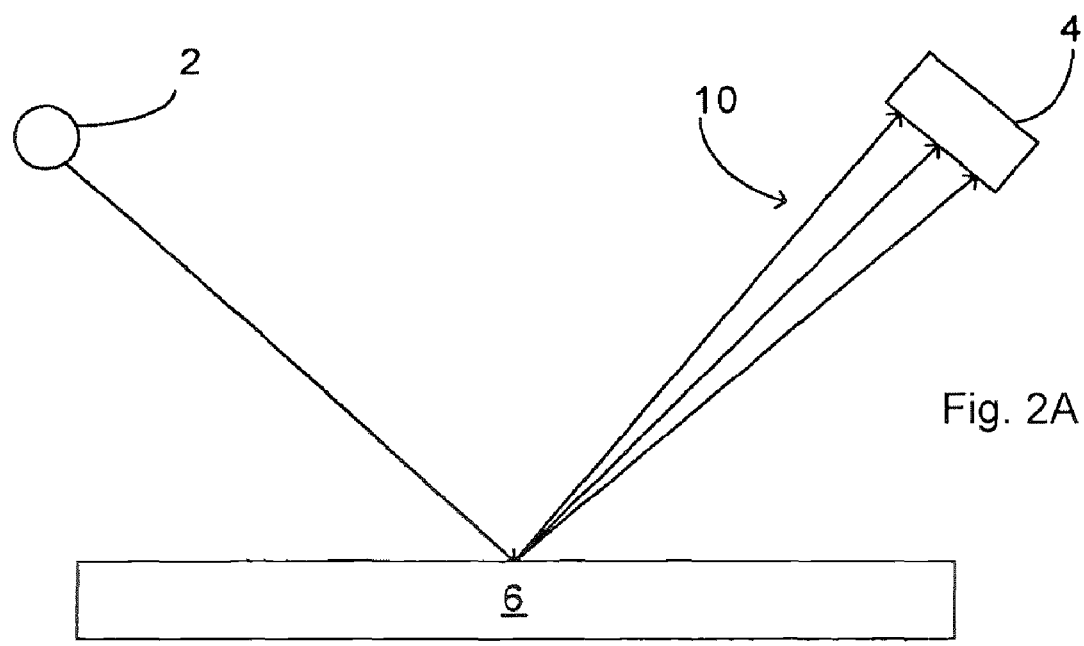
FIG. 2 depicts a scatterometer.
Figure 2B:
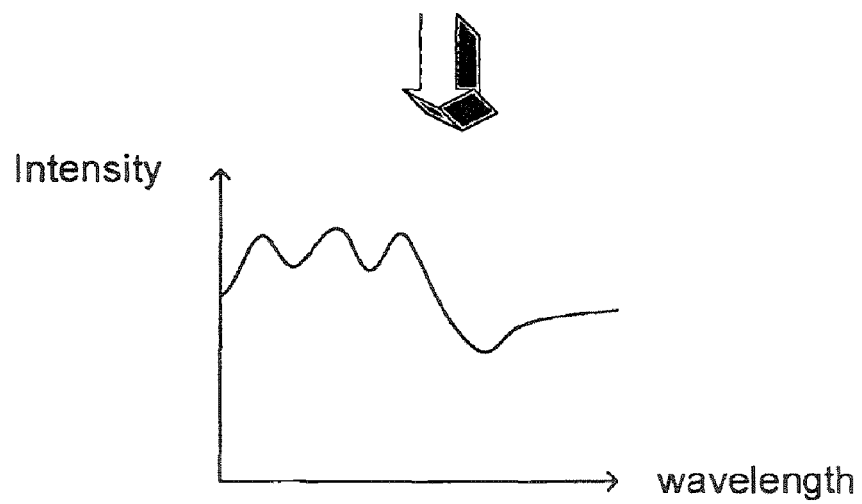
Figure 2C:
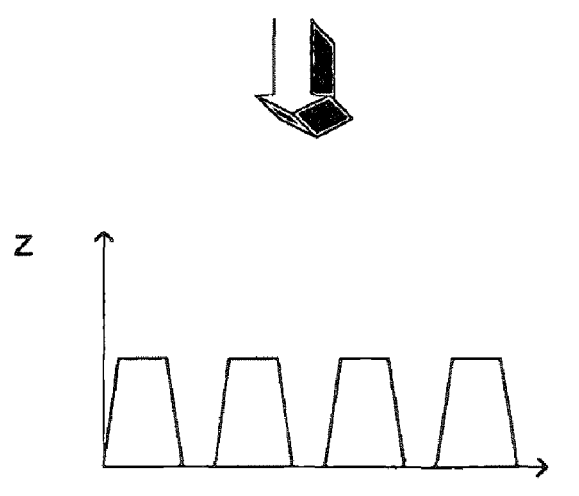

One or more properties of the surface of a substrate 6 may be determined using a scatterometer such as that depicted in FIG. 2. In an embodiment shown in FIG. 2A, the scatterometer comprises a broadband (white light) radiation source 2 which directs radiation onto a substrate 6. The reflected radiation is passed to a spectrometer detector 4, which measures a spectrum 10 (intensity as a function of wavelength) of the specular reflected radiation as shown in FIG. 2B. From this data, the structure or profile giving rise to the detected spectrum may be reconstructed, e.g. by Rigorous Coupled Wave Analysis and non-linear regression or by comparison with a library of simulated spectra as shown in FIG. 2C. In general, for the reconstruction, the general form of the structure is known and some parameters are assumed from knowledge of the process by which the structure was made, leaving only a few parameters of the structure to be determined from the scatterometry data.

The scatterometer may be a normal-incidence scatterometer or an oblique-incidence scatterometer. Variants of scatterometry may also be used in which the reflection is measured at a range of angles of a single wavelength, rather than the reflection at a single angle of a range of wavelengths.

In one or more embodiments described below, there is used a scatterometer configured to measuring a property of a substrate by measuring, in a pupil plane 40 of a high NA lens, a property of an angle-resolved spectrum reflected from the substrate surface 6 at a plurality of angles and wavelengths as shown in FIG. 3. The scatterometer comprises a radiation source 2 configured to project radiation onto the substrate and a detector 32 configured to detect the reflected spectra. The pupil plane is the plane in which the radial position of radiation defines the angle of incidence and the angular posit defines the azimuth angle of the radiation and any substantially conjugate plane (also known as the back focal plane). The detector 32 is placed in the pupil plane of the high NA lens. The NA is high and, in an embodiment, at least 0.9 or at least 0.95. Immersion scatterometers may even have lenses with a NA over 1.

Previous angle-resolved scatterometers have only measured the intensity of scattered light. An embodiment of the present invention allows several wavelengths to be measured simultaneously at a range of angles. The properties measured by the scatterometer for different wavelengths and angles may include the intensity of transverse magnetic (TM) and transverse electric (TE) polarized light and the phase difference between the TM and TE polarized light.

Using a broadband light source (i.e. one with a wide range of light frequencies or wavelengths—and therefore of colors) is possible, which gives a large etendue, allowing the mixing of multiple wavelengths. The plurality of wavelengths in the broadband light, in an embodiment, each has a bandwidth of, say, $\delta\omega$ and a spacing, therefore, of at least 2 $\delta\omega$ (i.e. twice the wavelength). Several "sources" of radiation can be different portions of an extended radiation source which have been split using, say, fiber bundles. In this way, angle-resolved scatter spectra can be measured at multiple wavelengths in parallel. A 3-D spectrum (wavelength and two different angles) may be measured, which contains more information than a 2-D spectrum. This allows more information to be measured which increases metrology process robustness.

A scatterometer of an embodiment of the present invention is shown in FIG. 3. The light source 2 is focused using lens system L2 through interference filter 30 and is focused onto substrate 6 via a microscope objective lens L1. The radiation is then reflected via partially reflective surface 34 into a detector 32 in the back projected pupil plane 40 in order to have the scatter spectrum detected. The pupil plane 40 is at the focal length of the high NA lens of the lens system L1. The detector 32 is placed at the pupil plane. Further, the pupil plane may be re-imaged with auxiliary optics where the pupil plane of a high NA lens is usually located inside the auxiliary optics.

The pupil plane of the reflector light is imaged on the CCD detector with an integration time of, for example, 40 milliseconds per frame. In this way, a two-dimensional angular scatter spectrum of the substrate target is imaged on the detector. The detector 32 may be, for example, an array of CCD detectors or CMOS detectors. The processing of the spectrum gives a symmetrical detection configuration and so detectors can be made rotationally symmetrical. This allows the use of a compact substrate table because a target on the substrate can be measured at any rotational orientation relative to the detector. All the targets on the substrate can be measured by a combination of a translation and a rotation of the substrate.

A set of interference filters 30 may be available to select a wavelength of interest in the range of, say, 405-790 nm or even lower, such as 200-300 nm. The interference filter may be tunable rather than comprising a set of different filters. A grating could be used instead of one or more interference filters.

The substrate 6 (or even the reflective surface 34) may be a grating. The grating may be printed such that after development, the bars are formed of solid resist lines. The bars may alternatively be etched into the substrate. This pattern is sensitive to comatic aberrations in a lithographic projection apparatus, particularly the projection system PL, and illumination symmetry and the presence of such aberrations will manifest themselves in a variation in the printed grating. Accordingly, the scatterometry data of the printed gratings is used to reconstruct the gratings. One or more parameters of the grating, such as line widths and shapes, may be input to the reconstruction process from knowledge of the printing step and/or other scatterometry processes.

In transmission metallic gratings with rectangular slits, complex photonic band structures (CPBS) are shown to exhibit strong discontinuities which are located on Wood-Rayleigh anomalies and reveal two types of resonance which are referred to as horizontal and vertical surface-plasmon resonances. Spectral position and width of peaks in the spectrum can be directly extracted from CPBS for both horizontal and vertical resonances. In this way, the radiation coming off a transmission metallic grating can have its spectrum analyzed and one or more properties of the grating determined by the strong discontinuities located on the Wood-Rayleigh anomalies. Wood-Rayleigh anomalies occur upon the variation of wavelength or angle of incidence, giving an additional propagating diffraction order. The greater the beam width, the greater the lateral displacement of the beam.

An embodiment of the present invention detects the spectrum and creates a symmetrical pupil plane image from which the discontinuities can be measured and one or more grating properties therefore calculated.

According to an embodiment of the invention, the scatterometer may be adapted to measure the overlay of two misaligned periodic structures by measuring asymmetry in the reflected spectrum, the asymmetry being related to the extent of the overlay.

In an embodiment, the scatterometer is adapted to measure the overlay of two misaligned gratings or periodic structures by measuring asymmetry in the reflected spectrum and/or the detection configuration, the asymmetry being related to the extent of the overlay. Thanks to the symmetrical detection configuration, any asymmetry is clearly distinguishable. This provides a straightforward way to measure misalignment in the gratings.

One type of substrate pattern used is shown in FIG. 4. A grating 14 has a second grating 12 printed on top of it. The amount by which the grating 12 is offset with respect to grating 14 is known as the overlay 22.

Figure 4A:
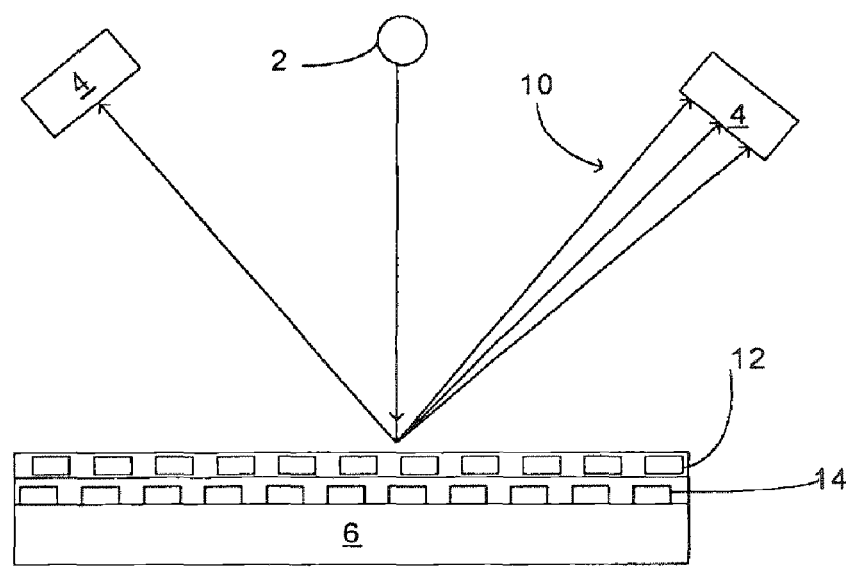
FIGS. 4A and 4B depict the use of an embodiment of the present invention in determining overlay.

Note that in the embodiment shown in FIG. 4A, the radiation source 2 illuminates the object symmetrically with respect to the surface normal and the scatterometry detector measures scatter radiation from several angles, although a source which illuminates the object from an oblique angle is also possible. However, due to an asymmetric target on the object, the radiation reflected is asymmetrical, as discussed below.

Overlay metrology is based on the measurement of an asymmetry in the angular scatter spectrum. Symmetric structures yield symmetric angular spectra and an asymmetry in the target shows up as an asymmetry in the angular scatter spectrum. This property is the basis of overlay metrology using angle-resolved scatterometry.

Figure 4B:
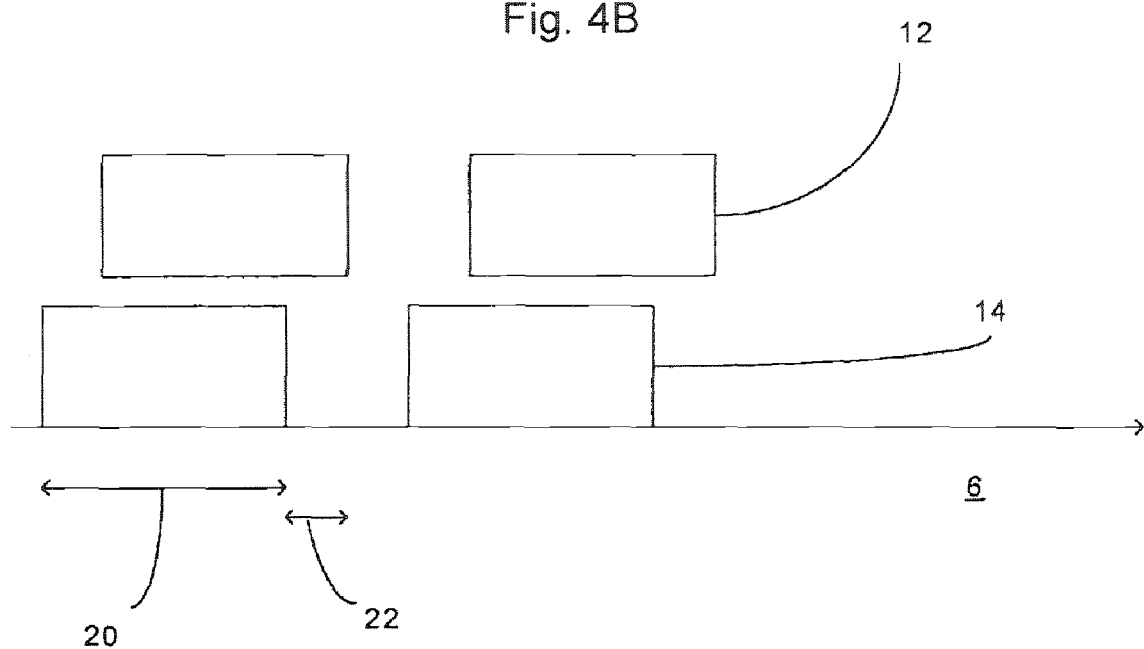

Two overlapping but misaligned gratings 12 and 14 made of bars with width 20 form one composite asymmetric target. The resulting asymmetry in the angular scatter spectrum is detected with the angle-resolved scatterometer 4 shown in FIG. 4A and used to derive the overlay 22 in the following manner:

Two grating pairs are used with a deliberate bias of +d and −d in, respectively, the first and second pair. In other words, grating 12 is shifted in one direction in one pair (as shown in FIG. 4B) and in the opposite direction in the other pair (not shown). The actual transverse shift between the gratings in each pair is therefore $X_1 = OV+d$ and $X_2 = OV-d$, OV being the overlay 22.

When the grating pairs are aligned, the overlay is 0 and if the intensity of the illumination incident on the gratings is $I_{ill}$ and the intensity of the radiation reflected off the gratings is $I_{+1}$ in a first direction and $I_{-1}$ in the opposite direction but in the same plane, when the overlay, $OV=0$, $$I_{+1} = I_{-1} \quad (1)$$

However, if $$OV \neq 0,$$

$$I_{+1} \neq I_{-1} \quad (2)$$

For a small overlay, the intensity difference is proportional to the overlay:

$$I_{+1} - I_{-1} = K \times OV. \quad (3)$$

K is a constant and is process dependent and therefore unknown.

In order to calibrate the overlay metrology with the scatterometer according to an embodiment of the present invention, two grating targets are used; one with the overlay shown in FIG. 4B and a second with the exact reverse overlay, so the upper grating 12 is displaced to the left rather than the right with respect to the bottom grating 14. The overlay in the first set-up is OV+d (distance 22 in FIG. 4B) and the overlay in the second set-up is OV−d.

So, for

OV+d, asymmetry $$A_+ = K(OV+d) \quad (4)$$

and for

OV−d, asymmetry $$A_- = K(OV-d). \quad (5)$$

The scaling factor K can be eliminated:

$$OV = d \frac{A_+ + A_-}{A_+ - A_-} \quad (6)$$

The overlay can therefore be calculated using measurements of the asymmetry in the angle-resolved scatter spectrum.

An advantage of this method compared to previously known methods is the fact that only two gratings are required. Moreover, in principle, the method can also work for 2-D gratings: in that case only 2 gratings are required for a complete (x,y) overlay measurement. This is a significant improvement compared to, say, 6 gratings that spectroscopic scatterometry methods use.

The analysis of xy overlay metrology using 2-D gratings is as follows:

Two gratings have an amplitude transmission of f(x, y) and g(x, y). These gratings are periodic in two directions and their transmissions can therefore be written as a Fourier series:

$$f(x, y) = \sum_n \sum_m F_{n,m} e^{-j(nx+my)} \quad (7)$$

$$g(x, y) = \sum_p \sum_q G_{p,q} e^{-j(px+qy)}$$

Both gratings have an equal period and for simplicity the periods of the gratings have been normalized to $2\pi$ for the following calculations. The coefficients $F_{n,m}$ and $G_{p,q}$ can be interpreted as diffraction efficiencies that depend on the grating shape, wavelength and polarization. The two gratings overlap with a relative overlay of $x_0$ and $y_0$ in, respectively, the x and y directions. The total transmission t can be written as:

$$t(x, y) = f(x, y) g(x - x_0, y - y_0) \quad (8)$$
$$= \sum_n \sum_m \sum_p \sum_q F_{n,m} G'_{p,q} e^{-j((p+n)x+(q+m)y)}$$

where:

$$G'_{p,q} = G_{p,q} e^{j(px_0+qy_0)} \quad (9)$$

The variables can be adjusted as follows:

$$p+n = a \Rightarrow p = a-n$$

$$q+m = b \Rightarrow q = b-m$$

Substituting these expressions in the Fourier series of t(x, y) yields:

$$t(x, y) = \sum_n \sum_m \sum_p \sum_q F_{n,m} G'_{n,m} e^{-j((p+n)x+(q+m)y)} \quad (10)$$
$$= \sum_a \sum_b T_{a,b} e^{-j(ax+by)}$$

where:

$$T_{a,b} = \sum_n \sum_m F_{n,m} G'_{a-n,b-m} \quad (11)$$

$T_{a,b}$ can be interpreted as the amplitude of the diffraction order (a,b). It can be see that this amplitude generally depends on the overlay in the x and y direction.

For simplicity, only diffraction orders running in the x-direction are considered. The analysis that follows can also be done for diffraction orders in the y-direction. This would only require an adjustment of variables.

For diffraction orders that run in the x-direction, b=0, so for the amplitude of two diffraction orders a and −a:

$$T_{a,0} = \sum_n \sum_m F_{n,m} G_{a-n,-m} e^{j((a-n)x_0 - my_0)} \quad (12)$$

$$T_{-a,0} = \sum_n \sum_m F_{n,m} G_{-a-n,-m} e^{j((-a-n)x_0 - my_0)}$$

taking the factor $e^{\pm jax_0}$ in front of the summation yields:

$$T_{a,0} = e^{jax_0} \sum_n \sum_m F_{n,m} G_{a-n,-m} e^{-j(nx_0 + my_0)} \quad (13)$$

$$T_{-a,0} = e^{-jax_0} \sum_n \sum_m F_{n,m} G_{-a-n,-m} e^{-j(nx_0 + my_0)}$$

$$= e^{-jax_0} \sum_{-n} \sum_m F_{-n,m} G_{-a+n,-m} e^{j(nx_0 - my_0)}$$

Assuming that both gratings are symmetric in the x-direction:

$$F_{-n,m} = F_{n,m}$$

$$G_{-n,m} = G_{n,m} \quad (14)$$

Using this property yields for the diffracted amplitudes:

$$T_{a,0} = e^{jax_0} \sum_n \sum_m F_{n,m} G_{a-n,-m} e^{-j(nx_0 + my_0)} \quad (15)$$

$$T_{-a,0} = e^{-jax_0} \sum_n \sum_m F_{n,m} G_{a-n,-m} e^{j(nx_0 + my_0)}$$

The scatterometer measures the intensities of the diffracted fields, giving:

$$I_{\pm a,0} = |T_{\pm a,0}|^2 \quad (16)$$

Evaluation of this expression shows that the intensity can be written in the form:

$$I_{a,0} = \sum_n \sum_m B_{n,m} \cos(\varepsilon_{n,m} - nx_0 - my_0) \quad (17)$$

$$I_{-a,0} = \sum_n \sum_m B_{n,m} \cos(\varepsilon_{n,m} + nx_0 - my_0)$$

where the amplitudes $B_{n,m}$ and phases $\varepsilon_{n,m}$ depend on the grating shapes, illumination wavelength and illumination polarization. Taking the difference of the +1 and −1 order yields an asymmetry $A_x$ that runs in the x-direction:

$$A_x = I_{1,0} - I_{-1,0} \quad (18)$$

$$= \sum_n \sum_m B_{n,m} \cos(\varepsilon_{n,m} - nx_0 - my_0) -$$

$$\sum_n \sum_m B_{n,m} \cos(\varepsilon_{n,m} + nx_0 - my_0)$$

$$= \sum_n \sum_m 2B_{n,m} \sin(\varepsilon_{n,m} - my_0) \sin(nx_0)$$

In practice the overlay is small compared to the pitch of the gratings. For example, the pitch is often of the order of 1 μm and the maximum overlay is of the order of 60 nm. The expression above can therefore be linearized and only the linear terms in $x_0$ and $y_0$ retained:

$$A_x = \sum_n \sum_m 2B_{n,m} \sin(\varepsilon_{n,m} - my_0) \sin(nx_0) \quad (19)$$

$$= \sum_n \sum_m 2B_{n,m} [\sin(\varepsilon_{n,m}) \cos(my_0) -$$

$$\cos(\varepsilon_{n,m}) \sin(my_0)] \sin(nx_0)$$

$$\cong \sum_n \sum_m 2B_{n,m} [\sin(\varepsilon_{n,m}) - \cos(\varepsilon_{n,m}) my_0] nx_0$$

$$= x_0 K_0 + K_{xy} x_0 y_0$$

where $$K_0 = \sum_n \sum_m 2n B_{n,m} \sin(\varepsilon_{n,m}) \quad (20)$$

$$K_{xy} = \sum_n \sum_m 2mn B_{n,m} \cos(\varepsilon_{n,m})$$

It can be seen that there is a coupling term: The asymmetry in the x-direction is also a function of the y-overlay via the coupling term $K_{xy}$. If the 2-D grating has 90° rotation symmetry and if the light is polarized at 45°, then we can write for the asymmetry in the x and y directions:

$$A_x = x_0 K_0 + K_{xy} x_0 y_0$$

$$A_y = y_0 K_0 + K_{xy} x_0 y_0 \quad (21)$$

These equations are the basis for xy overlay metrology with two 2-D grating pairs. In the first grating pair, a bias of +d is introduced in the upper grating and in the second grating pair, a bias of −d is introduced. This bias is applied in both the x and y direction. Four asymmetry terms can now be measured: An x and y asymmetry in the first grating pair and an x and y asymmetry in the second grating pair are shown as:

$$A_{1x} = K_0(OV_x + d) + K_{xy}(OV_y + d)(OV_x + d)$$

$$A_{1y} = K_0(OV_y + d) + K_{xy}(OV_y + d)(OV_x + d)$$

$$A_{2x} = K_0(OV_x - d) + K_{xy}(OV_y - d)(OV_x + d)$$

$$A_{2y} = K_0(OV_y + d) + K_{xy}(OV_y + d)(OV_x - d) \quad (22)$$

This gives four non-linear equations with four unknowns $K_0$, $K_{xy}$, $OV_x$ and $OV_y$, which can be solved to give the overlay.

In an embodiment, one or more apertures may be provided to the scatterometer to mimic lithography exposure conditions when the grating pattern(s) was created. The apertures may then be used in the creation of the angle-resolved spectroscopic image of the grating pattern(s) using the scatterometer.

In an embodiment, it is possible to immerse at least part of the space between the substrate and the detector in liquid, more specifically, the space between lens L1 and the substrate 6 as shown in FIG. 3. This has the advantage of increasing the spatial bandwidth of the medium between the substrate 6 and the lens L1. This means that a diffraction that would be evanescent, for example, in air can propagate and be captured by the lens. With immersion of the space, therefore, it becomes possible to detect a higher diffraction order that contains more detailed information about the grating under investigation than with, for example, air in the space.

Immersing the space between L1 and the object with a high refractive index fluid increases the spatial bandwidth of the medium and allows the propagation of a higher diffraction order for smaller pitches. The smallest pitch that creates a propagating first order spectrum is $$\frac{\lambda}{(2NA)}.$$

Assuming NA equals 1.3 and λ equals 400 nm, this yields a minimum pitch of 154 nm. This corresponds to a critical dimension (CD) or reconstructed grating width of approximately 20 to 80 nm. When looking at a profile such as that shown in FIG. 2C, the critical dimension is the mean width of a peak and the pitch is the distance from one peak to the next.

The immersion fluid should have a large index step with respect to, for example, the resist which is on the substrate 6. This may allow maximum contrast in the detector image. A possible liquid which fulfils such requirements is water.

Figures 5A, 5B:
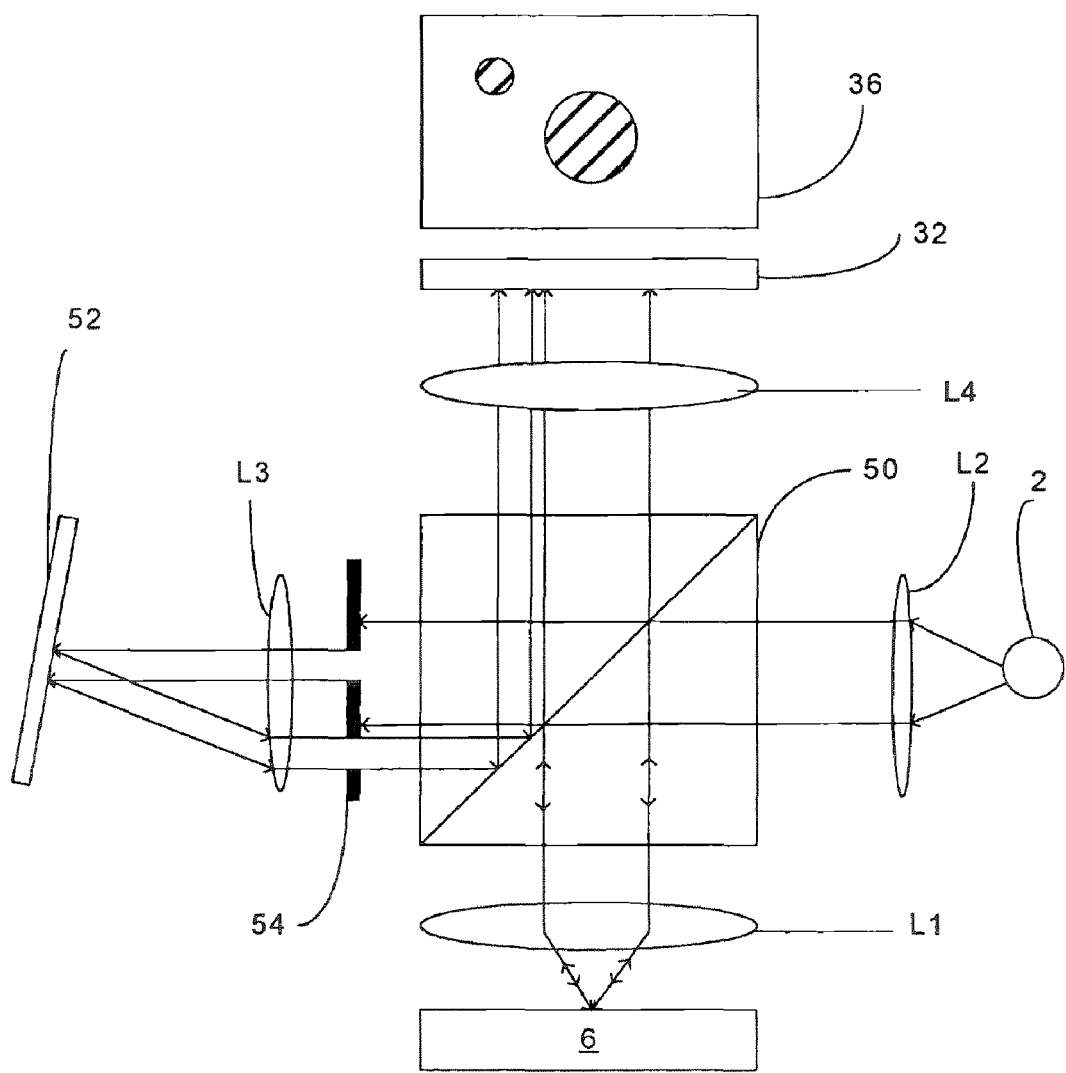
FIGS. 5A and 5B depict the use of a non-polarizing beam splitter for coupling off a portion of a radiation beam according to an embodiment of the invention.

FIG. 5A shows, according to an embodiment of the invention, the use of one and the same detector to monitor the source output intensity and the intensity of scattered radiation, which avoids synchronization problems and allows a real-time compensation for source output variations.

The scatterometer may comprise a non-polarizing beam splitter and a tilted mirror for coupling off a portion of the radiation beam emitted from the radiation source for separate measurement with the same detector. In an embodiment, the portion of the radiation beam is used to measure the intensity of the radiation beam and the scatterometer may be adapted to compensate for fluctuations in intensity of the radiation beam. Advantages of using the same CCD detector for the intensity measurement beam alongside the main measurement beam are that no extra detector is required and so there is no difference in optical and thermal properties between a reference detector and a metrology detector; and there are no extra electronics required to trigger, read out and store the reference signal. Any intensity variations may be measured and compensated for.

A non-polarizing beam splitter 50 in the radiation path images scattered radiation on a two-dimensional detector 32. An extra lens L4 re-images the pupil plane onto the detector 32. The intensity incident on the detector is shown as image 36. The non-polarizing beam splitter 50 also couples out a portion of the radiation beam to use it for monitoring intensity noise. Instead of measuring this radiation portion with a separate detector, the light is retro-reflected using tilted mirror 52 and transmitted to a separate part of the same detector 32. An optional pupil stop 54 limits the extent of the radiation portion and the mirror tilt ensures that the radiation portion is projected alongside the main radiation beam. The spectrum is imaged onto the detector 32 at the pupil plane of L1. FIG. 5B shows an elevation view of the detector 32.

In previous methods, angle-resolved scatterometry has been done at a single wavelength. Measurements at different wavelengths would then have been done sequentially and the different wavelengths would be time multiplexed. However, time multiplexing of the wavelengths may degrade throughput.

In an embodiment, the scatterometer comprises a wavelength multiplexer between the radiation source and the substrate and a demultiplexer between the substrate and the detector. This allows several different wavelengths (or colors) to be measured simultaneously, giving more information in a shorter time frame and therefore robustness as discussed above.

The surface area of the radiation source is preferably split into N parts that are each coupled to a wavelength multiplexer, where N is the number of discrete wavelengths. This splitting can be done, for example, with fiber bundles and the like.

In an embodiment, the multiplexer comprises a dispersive element placed at a back-projected object plane. The dispersive element may be a grating or prism adapted to accommodate N discrete wavelengths each with a bandwidth $\delta\omega$ and a spacing of at least twice the bandwidth i.e. $2\,\delta\omega$. This may maximize the usage of an extended light source. Measurement of different wavelengths no longer has to be time-multiplexed because it can be done at the same time, and so a major advantage is that throughput is increased.

In an embodiment, the demultiplexer comprises a dispersive element placed at a pupil plane. One or more optical wedges may be inserted in the object plane to achieve well-defined separation of angle-resolved spectra in the pupil plane.

In an embodiment, an extended broadband radiation source such as a xenon, deuterium or quartz tungsten halogen light source is used. These sources have a large etendue that gives a surface area that can be split into discrete wavelengths and offer more information as discussed above. The wavelengths may be in the range of 193 to 800 nm.

In an embodiment, a dispersive prism or grating which combines N discrete wavelengths is used in the illumination branch (or the radiation path between the source 2 and the substrate 6 in FIG. 2) and a grating or prism is used in the detection branch (or the space between the radiation path between the substrate 6 and the detector 4) to spatially separate the wavelengths.

An example of a multiplexing grating is shown in FIG. 6. Two light sources S1 and S2 are transmitted through a lens system L2 and strike a Littrow mounted grating 16 which is in the object plane 42 and are focused on the pupil plane 40 before being transmitted through a lens system L1 to another object plane 42 and optionally into an illumination fiber 60. The pupil plane contains rectangular apertures (not shown) of suitable dimensions—the width determining the angular extent of the light incident on the grating. This angular extent and the grating pitch determine the bandwidth of the returning light that is transmitted via the aperture in the pupil plane. For example, a grating with 1200 lines per millimeter yields a dispersion of approximately 1.2 mrad/nm. An effective bandwidth of 4 nm corresponds to a full angular width of the illumination beam of 3.33 mrad. The spot size of the substrate 6 is approximately 40 μm and its NA is 0.95. The beam diameter on the grating is therefore approximately 23 mm. If the focal length of the lens L1 is 100 mm, then the width of the aperture holes in the pupil plane must be 333 μm. If an illumination fiber is used, then the illumination NA must be approximately 0.22.

Clearly more than two radiation sources (with different wavelengths) may be used at a time.

Figure 7:
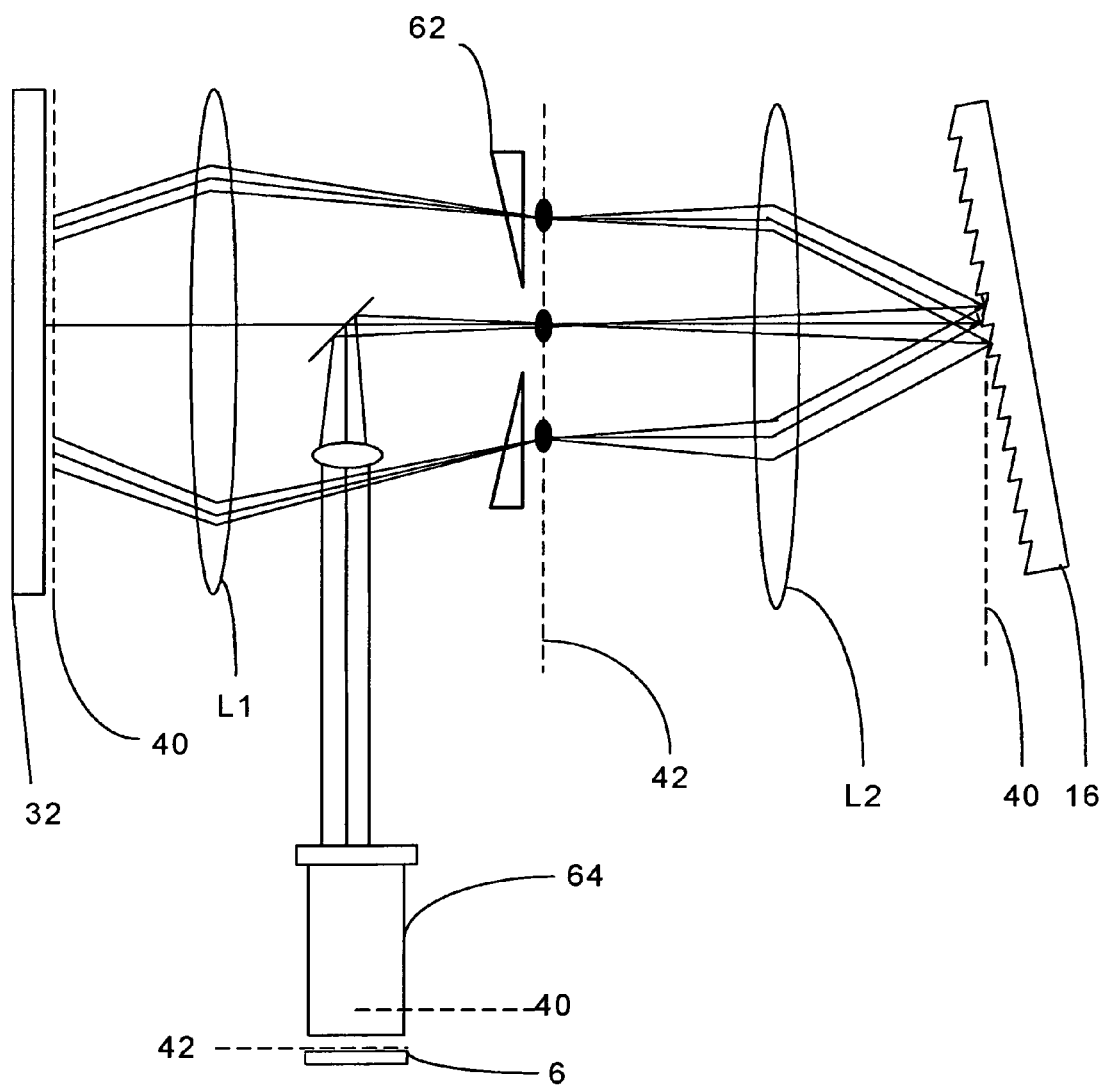
FIG. 7 depicts a wavelength demultiplexer according to an embodiment of the invention.

FIG. 7 shows an example of a wavelength demultiplexer in the detection branch, used in connection with a high Na lens 64 of the scatterometer. For simplicity, the separation of only two wavelengths is again shown. The demultiplexer is similar to the muliplexer, except that the grating is placed in the pupil plane and not in the object plane. The light that is diffracted by the grating in the Littrow mounted grating 16 is transmitted by the lens L2 which makes two object images with wavelengths λ1 and λ2 in the object plane 42. This object plane 42 may contain field stops with n holes (n=2 in this case), which should be sufficiently wide to avoid spatial filtering to avoid disturbing the spectrum. Each hole of the field stop also has a wedge 62 with a unique wedge angle. This wedge 62 ensures that the angle-resolved scatter spectrum for each wavelength is imaged on a different part of the CCD detector 32. The CCD detector is based at the second pupil plane 40.

Since the wedges 62 can deflect the light in two directions, it is possible to realize an efficient filling of a CCD detector with many angle-resolved spectra.

Figure 8:
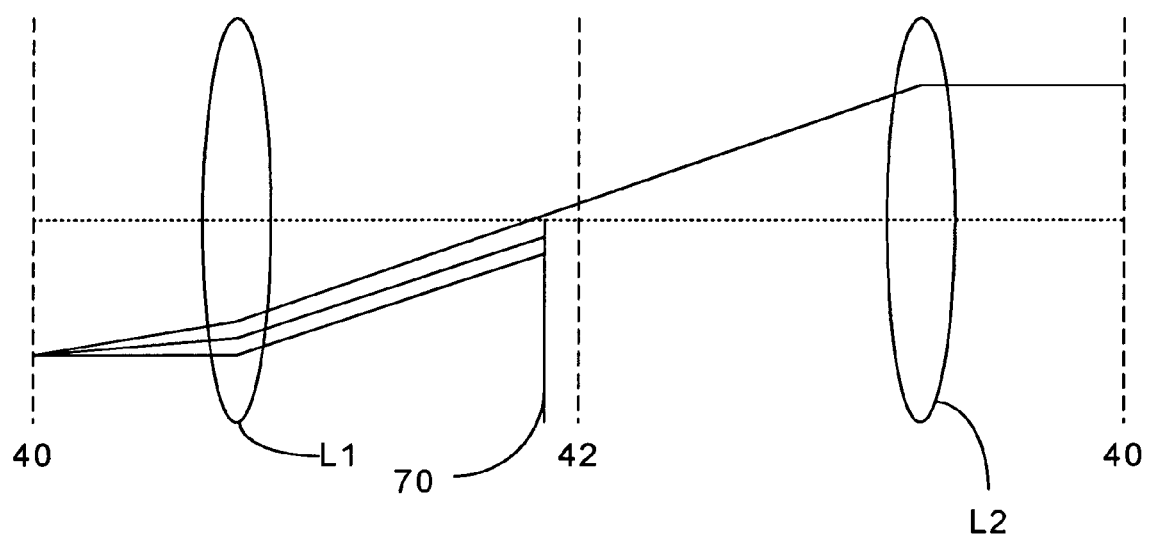
FIG. 8 depicts a knife edge at an intermediate object plane according to an embodiment of the invention.

In order to obtain reproducible results, the targets should be well focused. In order to achieve this, the pupil plane 40 of a high NA objective is imaged on a detector with a double telecentric system as shown in FIG. 8 according to an embodiment of the invention.

A knife edge 70 in the intermediate object plane 42 blocks one half of the intermediate object image. The edge may be a Foucault knife-edge.

The knife-edge helps to focus the image of the radiation onto the substrate. For each orientation, the intensity in the outer regions (or practically speaking, in two halves) of the pupil plane 40 is sampled. In the case of a defocus, a difference in intensities I1 and I2 is produced. Focus F is given as:

$$F = k \frac{I1 - I2}{I1 + I2} \quad (13)$$

The proportionality factor k is independent of the image and needs to be determined only once, though since the focus detector can be used in an integrating feedback loop, the precise value of k is not important.

While specific embodiments of the invention have been described above, it will be appreciated that the invention may be practiced otherwise than as described. The description is not intended to limit the invention. The specifically described embodiments are extensions to a general operating principle and are not necessarily mutually exclusive; they are all combinable in a single metrology tool to increase its effectiveness based on results seen at a detector as described above. Further, although the embodiments described herein relate to lithography applications, the hardware and applications are not limited to these. They may be used for other applications such as monitoring etch process steps and the like.

The invention claimed is:

1. A scatterometer, comprising:
a lens configured to direct a radiation beam from a radiation source toward a pattern formed on a substrate; and
a detector located in a pupil plane of the lens and configured to detect an angle-resolved spectrum of the radiation beam reflected from the pattern,
wherein a property of the substrate is measured using the detector by measuring asymmetries between intensities of corresponding diffraction orders diffracted from the pattern in the reflected angle-resolved spectrum.

2. The scatterometer according to claim 1, wherein a numerical aperture of the lens is at least 0.9.

3. The scatterometer according to claim 1, wherein a numerical aperture of the lens is at least 0.95.

4. The scatterometer according to claim 1, wherein the detector is configured to measure at least one of (a) an intensity of a transverse magnetic and a transverse electric polarized light and (b) a phase difference between the transverse magnetic and the transverse electric polarized light.

5. The scatterometer according to claim 1, wherein asymmetries between intensities of corresponding diffraction orders diffracted from the pattern are a property of the reflected angle-resolved spectrum, wherein the property of the substrate is further measured by measuring, in the pupil plane of the lens, another property of the reflected angle-resolved spectrum at a plurality of wavelengths substantially simultaneously.

6. The scatterometer according to claim 5, wherein the plurality of wavelengths each has a spacing of at least twice a bandwidth of the plurality of wavelengths.

7. The scatterometer according to claim 1, further comprising an extended broadband radiation source configured to provide the radiation beam to the surface of the substrate, the radiation beam having a wavelength of at least 50 nm.

8. The scatterometer according to claim 1, wherein the asymmetries are related to an extent of an overlay between two misaligned periodic structures.

9. The scatterometer of claim 1, further comprising a non-polarizing beam splitter and a tilted mirror configured to couple off a portion of the radiation beam emitted from a radiation source for a separate measurement with the detector.

10. A scatterometer, comprising:
a high numerical aperture lens configured to direct a radiation beam from a radiation source toward a substrate;
a detector located in a pupil plane of the high numerical aperture lens and configured to detect an angle-resolved spectrum of the radiation beam reflected a surface of the substrate; and
a wavelength multiplexer located between a radiation source configured to provide the radiation beam and the substrate and a wavelength demultiplexer located between the substrate and the detector,
wherein a property of the substrate is measured using the detector by measuring an asymmetry in the reflected angle-resolved spectrum at a plurality of angles substantially simultaneously.

11. The scatterometer according to claim 10, wherein the wavelength multiplexer comprises a dispersive element placed at a back-projected object plane.

12. The scatterometer according to claim 11, wherein the dispersive element is one of a grating and a prism adapted to accommodate N discrete wavelengths each having a spacing of at least twice a bandwidth of the plurality of wavelengths.

13. The scatterometer according to claim 10, wherein a surface area of the radiation source is split into N parts that are each coupled to the wavelength multiplexer, where N is a number of discrete wavelengths.

14. The scatterometer according to claim 10, wherein the wavelength demultiplexer comprises a dispersive element placed at the pupil plane.

15. The scatterometer according to claim 1, further comprising an optical wedge in an object plane configured to achieve a pre-defined separation of the reflected angle-resolved spectrum in the pupil plane.

16. The scatterometer according to claim 1, wherein a portion of the radiation beam is used to measure an intensity of the radiation beam.

17. The scatterometer according to claim 1, the detector is adapted to compensate for fluctuations in an intensity pattern of the reflected radiation beam.

18. The scatterometer according to claim 1, further comprising a pupil stop configured to limit a size of a portion of the radiation beam.

19. A scatterometer, comprising:
a lens configured to direct a radiation beam from a radiation source toward a pattern formed on a substrate; and
a space between the substrate and the lens comprising a liquid, wherein a property of the substrate is measured using a detector by measuring asymmetries between intensities of corresponding diffraction orders in an angle-resolved spectrum of a radiation beam diffracted from the pattern, at a plurality of angles and a plurality of wavelengths substantially simultaneously.

20. The scatterometer according to claim 19, wherein the liquid is water.

21. The scatterometer according to claim 19, wherein a numerical aperture of the lens is at least 0.9.

22. The scatterometer according to claim 19, wherein a numerical aperture of the lens is at least 0.95.

23. The scatterometer according to claim 19, wherein the detector is configured to measure at least one of (a) an intensity of a transverse magnetic and a transverse electric polarized light and (b) a phase difference between the transverse magnetic and the transverse electric polarized light.

24. The scatterometer of claim 19, further comprising a non-polarizing beam splitter and a tilted minor configured to couple off a portion of the radiation beam emitted from a radiation source for a separate measurement with the detector.

25. A scatterometer, comprising:
a high numerical aperture lens configured to direct a radiation beam from a radiation source toward a substrate;
a space between the substrate and the high numerical aperture lens comprising a liquid;
a wavelength multiplexer located between a radiation source, configured to provide the radiation beam, and the substrate; and
a wavelength demultiplexer located between the substrate and the detector located in a pupil plane of the high numerical aperture lens, and configured to measure another property of the reflected spectrum,
wherein a property of the substrate is measured using a detector by measuring an asymmetry in an angle-resolved spectrum of a radiation beam reflected from a surface of the substrate, at a plurality of angles and a plurality of wavelengths substantially simultaneously.

26. A scatterometer, comprising:
a lens configured to direct a radiation beam from a radiation source toward a pattern formed on a substrate; and
an edge adapted to be placed in one of opposite halves of an intermediate object plane associated with the lens,
wherein a property of the substrate is measured by a detector by measuring asymmetries between intensities of corresponding diffraction orders in an angle-resolved spectrum of a radiation beam diffracted from the pattern, at a plurality of angles and a plurality of wavelengths substantially simultaneously.

27. The scatterometer of claim 26, further comprising a non-polarizing beam splitter and a tilted mirror configured to couple off a portion of the radiation beam emitted from a radiation source for a separate measurement with the detector.

28. The scatterometer according to claim 26, wherein the edge is a Foucault knife edge.

29. The scatterometer according to claim 26, wherein a numerical aperture of the lens is at least 0.9.

30. The scatterometer according to claim 26, wherein a numerical aperture of the lens is at least 0.95.

31. The scatterometer according to claim 26, wherein wherein the detector is configured to measure at least one of (a) an intensity of a transverse magnetic and a transverse electric polarized light and (b) a phase difference between the transverse magnetic and the transverse electric polarized light.

32. A scatterometer, comprising:
a high numerical aperture lens configured to direct a radiation beam from a radiation source toward a substrate;
an edge adapted to be placed in one of opposite halves of an intermediate object plane associated with the high numerical aperture lens;
a wavelength multiplexer located between a radiation, source configured to provide the radiation beam, and the substrate; and
a wavelength demultiplexer located between the substrate and the detector located in a pupil plane of the high numerical aperture lens, and configured to measure the property of the reflected spectrum,
wherein a property of the substrate is measured by a detector by measuring an asymmetry in an angle-resolved spectrum of a radiation beam reflected from a surface of the substrate, at a plurality of angles and a plurality of wavelengths substantially simultaneously.

* * * * *

UNITED STATES PATENT AND TRADEMARK OFFICE
CERTIFICATE OF CORRECTION

PATENT NO. : 7,791,727 B2  Page 1 of 1
APPLICATION NO. : 10/918742
DATED : September 7, 2010
INVENTOR(S) : Den Boef et al.

It is certified that error appears in the above-identified patent and that said Letters Patent is hereby corrected as shown below:

Claim 31, col. 16, line 17, please delete "wherein"

Signed and Sealed this

Thirtieth Day of November, 2010

David J. Kappos
*Director of the United States Patent and Trademark Office*